(12) United States Patent
Lee et al.

(10) Patent No.: US 6,447,814 B1
(45) Date of Patent: Sep. 10, 2002

(54) CHINESE HERBAL COMPOSITION FOR IMPROVING BLOOD CIRCULATION AND THE METHOD OF PREPARING THE SAME

(75) Inventors: Fang-Yu Lee; Huan Wu; Ming Ching Chang, all of Taichung (TW)

(73) Assignee: Yung Shin Pharma Ind. Co. Ltd., Tachia (TW)

( * ) Notice: Subject to any disclaimer, the term of this patent is extended or adjusted under 35 U.S.C. 154(b) by 0 days.

(21) Appl. No.: 09/939,593

(22) Filed: Aug. 28, 2001

(51) Int. Cl.⁷ .......................... A01N 65/00; A61K 35/78
(52) U.S. Cl. ........................................................ 424/725
(58) Field of Search .............................. 424/725, 195.1, 424/728, 773, 774

(56) References Cited

U.S. PATENT DOCUMENTS 5,807,554 A * 9/1998 Yng-Wong .............. 424/195.1

FOREIGN PATENT DOCUMENTS

| CN | 1140064 A | * | 1/1997 |
| JP | 62221619 | * | 9/1987 |

* cited by examiner

Primary Examiner—Christopher R. Tate
Assistant Examiner—Patricia D Patten
(74) Attorney, Agent, or Firm—Fei-Fei Chao; Venable, Baetjer, Howard & Civiletti, LLP (57) ABSTRACT

The present invention provides an herbal composition for improving blood circulation and treating patients with coronary heart diseases and stroke. The herbal composition comprises 30–50 wt % of Dang Gui root (Radix Angelicae sinensis), 35–65 wt % of Chuan Xiong root (Radix Ligustici Chuanxiong), and 7–13 wt % of Ginseng root (Radix Ginseng). The present invention also provides methods of preparing the same.

27 Claims, 3 Drawing Sheets

CHINESE HERBAL COMPOSITION FOR IMPROVING BLOOD CIRCULATION AND THE METHOD OF PREPARING THE SAME

FIELD OF THE INVENTION

The present invention relates to a novel Chinese herbal composition for improving blood circulation and for treating patients with coronary heart diseases and stroke. The composition comprises 30–50 wt % of Dang Gui (Radix Angelicae sinensis), 35–65 wt % of Chuan Xiong (Radix Ligustici Chuanxiong), and 7–13 wt % of Renshen (Radix Ginseng), preferably Red Ginseng (Radix Ginseng Rubra). The present invention also relates to methods for preparing and using the same.

BACKGROUND OF THE INVENTION

The so-called blood stasis in Chinese medicine is generally referred to as an abnormal state in blood rheology where the blood tends to thicken, become viscous, coagulate and aggregate, or the condition of stagnant or discontinuous blood flow that leads to all kinds of disease symptoms. Blood stasis has been shown to be the main characteristic of at least one hundred types of disease, in particular, the cardiovascular and cerebroascular diseases.

A recent report published by the World Health Organization (WHO) indicates that cardiovascular disease has been the single greatest cause of death, with 15 millions of people dying from it every year worldwide. Among the cardiovascular and cerebrovascular diseases, coronary heart disease and stroke are particularly of concerns in most of the developed countries. The incidence of these diseases is increasing, while the onset age of the patients is decreasing.

Besides a few surgical adaptation approaches, the primary management of stroke and coronary heart disease still relies on drug treatments. In the early stage, the treatment focuses on decreasing the mortality rate and the occurrence of complications; later on, the treatment focuses on rehabilitation and the prevention of recurrence.

The commonly used medications include anti-coagulants, anti-thrombosis agents, vasodilators, medicines for enhancing cerebral metabolism, decreasing cerebral pressure, and blood pressure, and medicines for decreasing myocardial oxygen consumption and facilitating coronary blood flow. Although these medications have therapeutic effects, they tend to produce adverse effects or have diminished activity after prolonged use. This is particularly true for anti-coagulants, e.g., aspirin and/or ticlopidine, which are used to prevent cerebrovascular diseases. Also, although these drugs can improve blood circulating, they have adverse side effects on humans. Aspirin has been shown to affect appetite, cause stomachache, gastric ulcer and even bleeding. In some cases, aspirin has also been found to induce asthma. Ticlopidine can cause nausea, dullness, headache, palpitation, fatigue, liver disorder, jaundice, bleeding tendency, and abnormal blood formation, leading to decreased platelet count, granulocytopenia and even anemia due to blood regeneration failure. More importantly, these medications only control the symptoms of the diseases without having any effect on the pathogenesis of the diseases.

In recent years, there have been studies which demonstrated that sex hormone disturbance is a common cause of many frequently seen diseases found in the middle-aged and the elderly, including coronary heart disease, angina pectoris, myocardial infarction, hypertension, diabetes, sinoatrial nodal dysfunction and so on. In males, the regular pattern of disturbance entails the increase of plasma estradiol (E2) level, while the level of testosterone (T) remains unchanged or decreases, resulting in elevated E2/T ratio. In females, both the E2 level and T level decrease. Aspirin and ticlopidine are ineffective for the disorders described above. Some alternative herbal medicines, such as gingko or its derived products have also been shown to improve blood circulation in clinical applications, but they fail to improve the conditions of sex hormone disturbance.

Thus, finding a medication, which can improve cardiovascular functions, regulate the levels of sex hormones, prevent cardiovascular diseases, and help slow down the aging process so as to improve and preserve health, is a pressing task, especially in an aging society.

In the invention to be presented in the following sections, a novel herbal composition for treating patients with invigorating blood and expelling stasis will be introduced. This herbal composition is particularly effective on treating patients with blood stasis while in the meantime having common and recurrent clinical diseases. The present invention can also be used to prevent many common diseases found in the middle-aged and the elderly.

SUMMARY OF THE INVENTION

The present invention provides a novel herbal composition for improving blood circulation and treating patients with coronary heart disease and stroke. This herbal composition has been shown to be safe and reliable by having consistent active ingredient(s) and enhanced therapeutic effects, with minimal side effects. The present invention also provides methods for making the same. The therapeutic effects of the herbal composition have been demonstrated successful in human subjects.

The herbal composition contains (a) 30–50 wt %, preferably 33–45 wt %, of Dang Gui root (Radix Angelicae sinensis); (b) 35–65 wt %, preferably 42–58 wt %, of Chuan Xiong root (Ligustici Chuanxiong), and (c) 7–13 wt %, preferably 8–12 wt %, of Renshen root (Radix Ginseng), also known as Ginseng root. The preferred Ginseng is Red Ginseng (Radix Ginseng Rubra). The herbal composition is preferably administered orally.

Dang Gui root, Chuan Xiong root, and Ginseng root are extracted with an extractant. The extracts of the herbs are filtered, condensed, and granulated to form granules. The granules can be further encapsulated.

The preferred extractant is alcohol and water, particularly 60% alcohol.

The present invention also provides methods for preparing the herbal composition: (1) combined herbal extraction; and (2) single herbal extraction.

The method for preparing combined herbal extraction contains the following steps: (a) mixing Dang Gui root, Chuan Xiong root, and Ginseng root in an extraction tank to form an herbal mixture; (b) adding an extractant to the herbal mixture to form an herbal mixture extract; (c) heating the herbal mixture extract; (d) filtering the heated herbal mixture extract to obtain a filtrate; (e) putting the filtrate into a condensation tank for decompressed condensation to obtain an extraction paste; and (f) granulating the extraction paste to form granules.

Dang Gui root, Chuan Xiong root and Ginseng root are preferred to be ground into powder or cut into small pieces before mixing together in the extraction tank.

The heating condition is preferred to be at about 70–80° C. for about 4 hours.

After extracting, heating and filtering of the herbal mixture, optionally, the herbal mixture can be extracted and filtered for a second and third times by repeating steps (b)–(d). The second and third filtrates can be combined with the filtrate and subject to decompressed condensation. Preferably, the extraction paste (i.e., the condensate) is about 1/10 by volume of the filtrate. Also preferably, the extraction paste is mixed with a soluble starch before granulation. The granulation is proceeded with a heat-dry step using a fluidized bed. The granules produced by the granulation process can be further capsulated.

The extraction paste contains 0.5 to 2.8 mg of ferulic acid per gram of the extraction paste and 0.2 to 1.6 mg of tetra-methyl pyrazine per gram of the extraction paste. The granules contain 0.08 to 0.42 mg of ferulic acid per gram of the granules and 0.04 to 0.25 mg of tetra-methyl pyrazine per gram of the granules.

The method for preparing single herbal extraction is as follows: (a) extracting Dang Gui root, Chuan Xiong root, and Ginseng root by adding an adequate amount of extractant to Dang Gui root, Chuan Xiong root, and Ginseng root respectively to form individual extracts; (b) heating the individual herb extracts; (c) filtering the heated individual herb extracts to obtain individual filtrates; (d) mixing the individual filtrates together to form a final filtrate; (e) putting the final filtrate into a condensation tank for decompressed condensation to obtain an extraction paste; and (f) granulating the extraction paste to form granules.

The preferred extractant is alcohol and water and most favorably 60% alcohol.

The heating condition is preferred to be at about 60–70° C. for about 4 hours.

After extracting, heating and filtering of the individual herb, optionally, the individual herb mixture can be extracted and filtered for a second and third times by repeating steps (a)–(c). The second and third filtrates can be combined with the individual filtrate altogether to form the final filtrate, which is subjected to decompressed condensation.

Preferably, the extraction paste is about 1/10 by volume of the filtrate. Also preferably, the extraction paste is mixed with a soluble starch before granulation. The granulation is proceeded with a heat-dry step using a Fluidized bed. The granules produced by the granulation process can be further encapsulated.

Finally, the present invention provides a method for improving blood circulation by orally administering an effective amount of the herbal composition described above to patients. This herbal composition also has efficacy for use in treating patients with coronary heart diseases and stroke.

The extraction paste contains 0.5 to 2.8 mg of ferulic acid per gram of the extraction paste and 0.2 to 1.6 mg of tetra-methyl pyrazine per gram of the extraction paste. The granules contain 0.08 to 0.42 mg of ferulic acid per gram of the granules and 0.04 to 0.25 mg of tetra-methyl pyrazine per gram of the granules.

BRIEF DESCRIPTION OF THE DRAWING

FIG. 1 shows the chronic toxicity test of the herbal composition using Wistar rats.

FIG. 2 shows the chronic toxicity test of the herbal composition using Wistar rats. The rats were given 0, 12 mg/kg, 60 mg/kg, and 300 mg/kg of the herbal composition for 90 days. The results show that in the control group, the number of platelets ($X\ 10^{10}$/L) increased for the first 60 days and slightly decreased thereafter. In the experimental groups being given 12 mg/kg and 60 mg/kg of the herbal composition, the number of platelets slightly increased during the first 30 days, dropped to the lowest amount at day 60, but gradually returned to normal at day 90. In the experimental group being given 300 mg/kg of the herbal composition, the number of platelet never increased. Between day 30 and day 60, the number of platelets in the 300 mg/kg group was about 40% of that of the control group. The results demonstrate that the herbal composition has the effects of lowering the number of platelets in the animals, the higher the dosage, the better the platelets lowering effects.

DETAILED DESCRIPTION OF THE INVENTION

Nourishing the kidneys and invigorate the blood circulation have been the main stream for preserving the health of the middle-aged and the elderly in the history of Chinese medicine. Nourishing the kidneys is the main approach for treating the disorders and dysfunction of the endocrine system, the reproductive system, the urinary system, the nervous system, the skeletal system and the metabolic system.

To invigorate blood circulation is the approach for treating blood stasis. The so-called blood stasis in the Chinese medicine has a broader scope than the congestion described in the modern medicine. It is referred to as any abnormality of the "blood path" which comprised heart, blood pressure, blood vessels, and blood. These abnormalities include disease-contaminated blood, stagnant or irregular blood flow and the escaped blood, blood with changed rheology or hemodynamics, and blood with thickening, viscous, coagulating and aggregating tendencies. Clinical blood stasis is the primary symptom for more than one hundred diseases.

Stroke and coronary heart diseases are categorized under "apoplexy" and "chest paralysis" in Chinese medicine. The development for their treatment in Chinese medicine can be divided into several stages. From the time the oldest medical book "Nei Jing;" was published in China to the couple hundred years after that, these diseases were treated with medications that nourish and benefit the qi (vital energy) and blood as well as expel winds and remove dampness.

After the Jing Dynasty and Yuan Dynasty, due to the prevailing theory for disease-origination, the treatment methods focused on nourishing yin and preserving the blood as well as soothing the liver and expelling the wind. At the end of the Chin Dynasty, Jung-Chuan Tang and Chin-Zen Wang proposed the concept of "blood stasis." Because of the introduction of blood rheology and hemodynamics, the theory of blood stasis has been proven by quantified figures. Therefore, modem approach in Chinese medicine still focuses on invigorating blood and dispelling stasis.

Inspired by the ancient "blood stasis" concept and the modem "sex hormone disorder" concept, the inventors of the present invention has continued the ideas of "the older, the weaker and the older, the more blood stasis" and "the sicker, the weaker and the sicker, the more blood stasis" in Chinese medicine and has thus proposed the way for healthy living by nourishing the kidneys and invigorating the blood.

This method has demonstrated significant positive results in treating the common and recurrent diseases in the middle-aged and the elderly, in particular, for the prevention and treatment of coronary heart disease and stroke.

Because blood stasis has been the main symptom for the common and recurrent diseases in the middle-aged and the elderly, the kidney nourishment and blood invigoration have broad applications in the health preservation and the prevention of cardiac and cerebral vascular diseases. Not only can it be used as a treatment approach, it is also a way to prevent diseases and regain health.

Base on the requirements for nourishing the kidneys and invigorating the blood, the present invention provides a novel formulation using Chinese herbs. The herbal composition of the present invention had effects on cardiac and cerebral vascular diseases. Its effects on angina in coronary heart disease, myocardial infarction, embolic stroke, TIA have been confirmed with experimental studies and clinical trials. The present herbal composition, when taken after the bleeding ceases in a hemorrhage stroke, also improves the absorption of the blood clots.

Improvements in circulation can benefit the rehabilitation and prevent the dementia caused by stroke or the recurrence of stroke. Cardiac and cerebral vascular diseases often are diseases with deficient origin and solid symptoms, the main solid symptom is blood stasis, while the deficiency nature is kidney deficiency. Therefore, using the herbal composition of the present invention as a prophylactic approach can dramatically enhance the therapeutic effect, limit the duration of diseased state. The effects are even more significant in patients with severe symptoms.

The herbal composition of the present invention uses Chuan Xiong (Radix Ligustici Chuanxiong) as the main ingredient for its properties of suppressing platelet function to improve the tendencies of concentration, viscosity, coagulation, and polymerization of the blood and to improve the micro- and systemic circulation, and its anti-thrombosis and thrombus-dissolving function.

Chuan Xiong has a very strong effect on invigorating blood and dispelling stasis. However, its pungent-spicy property and the warm and dry nature are not good at nourishing and preserving blood. Its long-term intake in a large amount might be harmful for the yin components of the body. Therefore, the dosage can not be too high for long-term application. Chuan Xiong can be found many provinces of China, such as Sichuan, Guizhou, Yunnan, Shaanxi, and Hubei. The therapeutic effect of Chuan Xiong is in its root. The root of Chuan Xiong is preferably to be harvested in summer when stems of the plant have a purple hue and the node of stem becomes obviously swollen.

However, the medication may not fulfill its functions if the dosage of Chuan Xiong is too small. Thus, the herb with similar functions, Dang Gui (Radix Angelicea sinensis) was added as a supplement to advance the effects of Chuan Xiong. Dang Gui is also an herb which is good for invigorating blood, nourishing blood and preserving blood, but gentler in actions. Dang Gui can be found in many provinces of China, in particular, Gansu, Sichuan, Shaanxi, and Hubei. The therapeutic effect of Dang Gui is in its root. The best harvest season for Dang Gui is at the end of autumn.

Dang Gui has long been used in blood diseases and female diseases. With the addition of Dang Gui, the amount of Chuan Xiong may be reduced, thus limiting the pungent-spicy and dryness of Chuan Xiong and the application of the formulation may be broadened to the conditions of yin deficiency and blood deficiency. Dang Gui can further enhance the therapeutic effect of Chuan Xiong and generate synergistic effect in invigorating blood.

Ginseng (Radix Ginseng), particularly Red Ginseng (Radix Ginseng Rubra), is added to supplement qi, invigorate blood, benefit the five solid organs, tonic yang, retard aging process, regulate the endocrine system, promote immune function, improve metabolism, postpone the aging of the reproductive system, promote brain function, strengthen the body and boost energy, endurance, mind strength, and sexual ability.

Ginseng is the dried root of Panax ginseng C. A. Mey. (Family: Araliaceae). The drug derived from the cultivated form is known as "Yuanshen" (Garden Ginseng) and the drug derived from the wild origin is known as "Shanshen" (Wild Ginseng). The drug is collected in autumn and washed clean, sun-dried or bake dried. Yuanshen is known as "Shengshaishen" (Sun-dried Ginseng). After steamed-dried, Yuanshen is known as "Hongshen," also known as "Red Ginseng."

With Dang Gui, Chuan Xiong and Ginseng to supplement qi, the prescription is aimed for invigorating blood and is more suitable for the middle-aged and the elderly to tonic blood, invigorate blood and preserve health. The present formulation designed based on this idea features refined ingredients, careful composition, significant effect and broad application, and can be considered as the basic formula for invigorating blood and dispelling stasis, and for promoting the circulation of qi.

The Families, pharmacopeia names, botanical names and common names of Dang Gui, Chuan Xiong, and Ginseng (including Red Ginseng), and the common descriptions and major known ingredients of the herbs is shown below:

| Pharmacopeia Name | Botanical Name | Family | Common Name | Major known Ingredients |
| --- | --- | --- | --- | --- |
| Radix Angelicae Sinensis | Angelica sinensis (Oliv.) Diels | Umbelliferae | Chinese Angelica root, Dang Gui | Ferulic acid n-butyl phthalide, ligustilide, n-butylidene-phthalide, carvacrol, sucrose, vitamin $B_{12}$, carotene, β-sitosterol (root) |
| Rhizoma Chuanxiong | Ligusticum chuanxiong Hort.; | Umbelliferae | Chuan Xiong | tetramethyl-pyrazine, perlolyrine, ferulic acid, chrysophanol, sedanonic acid, 4-hydroxy-3-butyphthalide Butylphthalide, Ligustilide, (Rhizome) |
| Radix Ginseng | Panax ginseng C.A. Mey. | Araliaceae | Renshen, Ginseng | Gins enosid, Rb1,Rb2, Rb3,Re,Rd, Rg3,Rg2,Re, Rh1 (root) |

In addition, the present invention provides for a product with stable quality, which is controlled by scientific method, good agriculture practices, and good manufacturing practices. Its therapeutic effect and safety have been confirmed in animal studies and in human clinical trials. The manufacturing process follows the regulations in America, Japan, and developed European countries to stay in line with the spirit of scientifising Chinese medicine.

To identify the basic properties of the herbs used in the present invention, the main ingredient, Chuan Xiong, was collected from 37 different producing areas. The samples were dissolved in methanol, extracted by ultra-sound for 30 minutes and analyzed with TLC to determine their ferulic acid content. It was discovered that Chuan Xiong collected from different areas demonstrated huge differences in the content of ferulic acid. The lowest ferulic acid content was 0.05167% and the highest was 0.13445%. After more than two years of observation, the best producing area and the best harvesting time were determined to meet the requirement for quality stability and consistency. The establishment of the inspection specifications and method for raw material inspection was also important. Both single-herbal and combined-herbal extractions were used in the process to search for convenient and stable formulation and the most suitable excipient to meet the requirements of stability, effectiveness, safety and good quality. In addition to the inspection of the herbal materials and the quality control of the product, the production control also followed the good manufacturing practices for drugs.

The main symptoms of the so-called blood stasis in Chinese medicine are changes in hemodynamics and blood rheology and the abnormalities in blood fluidity and viscosity. The basic pathophysiological characteristic is the abnormal circulation of blood in the vessels that results in an inadequate distribution of blood in some tissues and organs. The outcomes are systemic or local bruises and the consequent metabolic disorders or dysfunction of these tissues or organs. To improve blood circulation by influencing the parameters in blood rheology and improving the tendencies of concentration, viscosity, coagulation and polymerization can be protective for vascular, cellular, or tissue damage caused by acute ischemia. To affect the levels and activities of factors like thromboxane A2 (TXA2), prostaglandin 2 (PGI2), β-thromboglobin (β-TG) and platelet factor IV are also beneficial for blood circulation.

The present invention is further depicted with the illustration of the material control and quality control of the herbal composition, the safety test results of the herbal composition, and the efficacy studies of the herbal composition as follows:

I. Material Control and Quality Control
1. Material Control
   Specifications for material control
   (A) Dang Gui
   (1) Add 1.0 g of Dang Gui powder into 10 ml of methanol and extracted by ultrasound for 30 minutes. Filter the solution and subject the filtrate and ferulic acid standard to TLC and UV for qualitative analysis.
   (2) Subject the filtrate and ferulic acid standard to HPLC comparative analysis. The concentration of ferulic acid in the filtrate may not be lower than 0.02% (w/v).
   (3) The specifications for Dang Gui are as follows: After the sample has been dried under 105° C. for 5 hours, its weight loss might not exceed 13.0%, total ash may not be over 7.0%, acid-insoluble ash may not be over 1.0%, and diluted ethanol extract may not be less than 40%.
   (B) Ginseng
   (1) By the criteria provided in The Chinese Pharamacopia, add 1.0 g of ginseng powder into 10 ml methanol and extracted by ultrasound for 30 minutes. Filter the solution and subject the filtrate and ginseng saponin standard to TLC for qualitative analysis.
   (2) Subject the filtrate and ginseng saponin standard to HPLC comparative analysis. The concentration of ginseng saponin in the filtrate may not be lower than 0.1% (w/v).
   (C) Chuan Xiong
   (1) Add 1.0 g of Chuan Xiong powder into 10 ml of methanol and extracted by ultrasound for 30 minutes. Filter the solution and subject the filtrate and ferulic acid standard to TLC and UV for qualitative analysis.
   (2) Subject the filtrate and ferulic acid standard to HPLC comparative analysis. The concentration of ferulic acid in the filtrate may not be lower than 0.02% (w/v).
   (3) Subject the filtrate and tetra methyl pyrazine standard to comparative analysis. The concentration of tetra methyl pyrazine in the filtrate may not be lower than 0.005% (w/v).
   (4) The specifications for Chuan Xiong are as follows: After the sample has been dried under 105° C. for 5 hours, its weight loss might not exceed 13.0%, total ask may not be over 6.0%, and acid-insoluble ash may not be over 1.0% (w/v).
2. Quality Control
   For quality control, the specifications for the present inventions were as follows:
   a. The Extraction Paste
   The concentrations of ferulic acid and tetra-methyl pyrazine in the extraction paste were separately determined. For ferulic acid, one (1) gram of the extraction paste was dissolved in 25 ml of methanol. The dissolved extraction paste was filtered and the filtrate was injected into a high performance liquid chromatography (HPLC) and compared with the ferulic acid standard to determine the concentration of ferulic acid in the extraction paste. The amount of ferulic acid in the extraction paste which met the quality requirement was between 0.5 and 2.8 mg of ferulic acid per gram of the extraction paste.

For tetra-methyl pyrazine, one (1) gram of the extraction paste was dissolved in 25 ml of methanol. The dissolved extraction paste was filtered and the filtrate was injected into a high performance liquid chromatography (HPLC) and compared with the tetra-methyl pyrazine standard to determine the concentration of tetra-methyl pyrazine in the extraction paste. The amount of tetra-methyl pyrazine in the extraction paste which met the quality requirement was between 0.20 and 1.6 mg of tetra-methyl pyrazine per gram of the extraction paste.
   b. The Granules
   The concentrations of ferulic acid and tetra-methyl pyrazine in the granules were separately determined. For ferulic acid, three (3) grams of the granules were dissolved in 25 ml of methanol. The dissolved extraction paste was filtered and the filtrate was injected into a high performance liquid chromatography (HPLC) and compared with the ferulic acid standard to determine the concentration of ferulic acid in the granules. The amount of ferulic acid in the granules which met the quality requirement was between 0.08 and 0.42 mg of ferulic acid per gram of the granules.

For tetra-methyl pyrazine, three (3) grams of the granules were dissolved in 25 ml of methanol. The dissolved granules were filtered and the filtrate was injected into a high performance liquid chromatography (HPLC) and compared with the tetra-methyl pyrazine standard to determine the concentration of tetra-methyl pyrazine in the granules. The amount of tetra-methyl pyrazine in the granules which met the quality requirement was between 0.04 and 0.25 mg per gram of the granules.

In conclusion, to achieve the optimal therapeutic activity, the amount of ferulic acid in the final product (granules) may not be lower than 0.08 mg per gram of the granules, and that of tetra-methyl pyrazine may not be lower than 0.04 mg per gram of the granules. Also, the disintegration time of the final product should be less than 10 minutes, and water content should be less than 10%. In addition, the level of lead must be below 20 ppm and the level of arsenic must be below 10 ppm.

II. Safety Tests

The experimental designs and results of acute and chronic toxicity tests are shown below:

1. Experimental Design

A. Test for Acute Toxicity

Thirty (15 males and 15 females) healthy Kun-Ming mice, with weight of 17–22 g, were fasted for 12 hours and then treated with the present invention at a dosage that is 200 folds of the daily dose for an adult. The mice were given one single dose by gavage according to their weight (0.6 g of the product for every 20 g of the body weight was dissolved in a small amount of water and administered by gavage) and observed for seven days. All 30 mice stayed alive, healthy and active after the treatment and had regular appetite, urination and bowl movement. No adverse effect was observed. The animals were sacrificed at the end of the experiments. Visual examination of the heart, liver, spleen, lung and kidney did not find any abnormality.

B. Test for Chronic Toxicity

The chronic toxicity test aims to study whether long-term administration of the medicine at small dosage will produce toxic effects on the morphology and functions of the organs so as to ensure the safety of the medicine.

Eighty healthy and active Wistar rats at the age of six weeks were used after raising for one week. The rats were randomly divided into four groups (with 10 males and 10 females in each group). Three groups of the rat were administrated with the herbal composition of the present invention at doses that were 4 folds, 20 folds and 100 folds of the daily 9 g recommended for a human adult, i.e., 12 mg/kg, 60 mg/kg, 300 mg/kg, respectively. The medicine was dissolved in a small amount of distilled water and administrated to the rats daily by gavage before the first feeding in the morning for 60 days consecutively. The same amount of distilled water was given to the control group. The dosage was adjusted according to the weight of the rats every 15 days. The general characteristics, morphology, behavior, water intake, food intake of the rats were observed. Blood was sampled from the tail on day 0, 30, 60, and 90 for regular blood test and biochemical tests. Rats were sacrificed on day 60 and day 90 for general and microscopic pathological examination.

2. Results

Figure 1A:
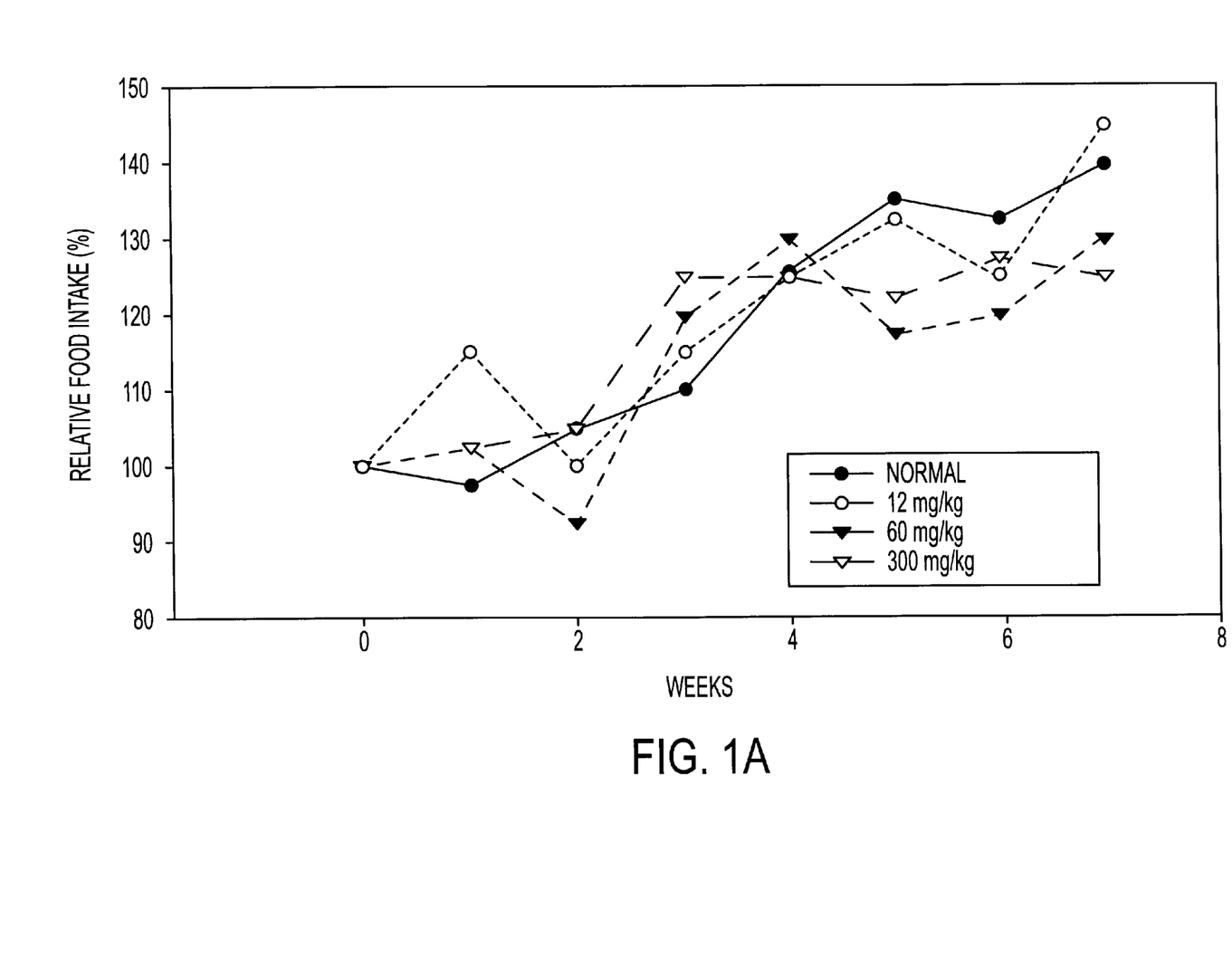
FIG. 1A shows the relative food intake (%) in the rats after being given 0, 12 mg/kg, 60 mg/kg, and 300 mg/kg of the herbal composition.
Figure 1B:
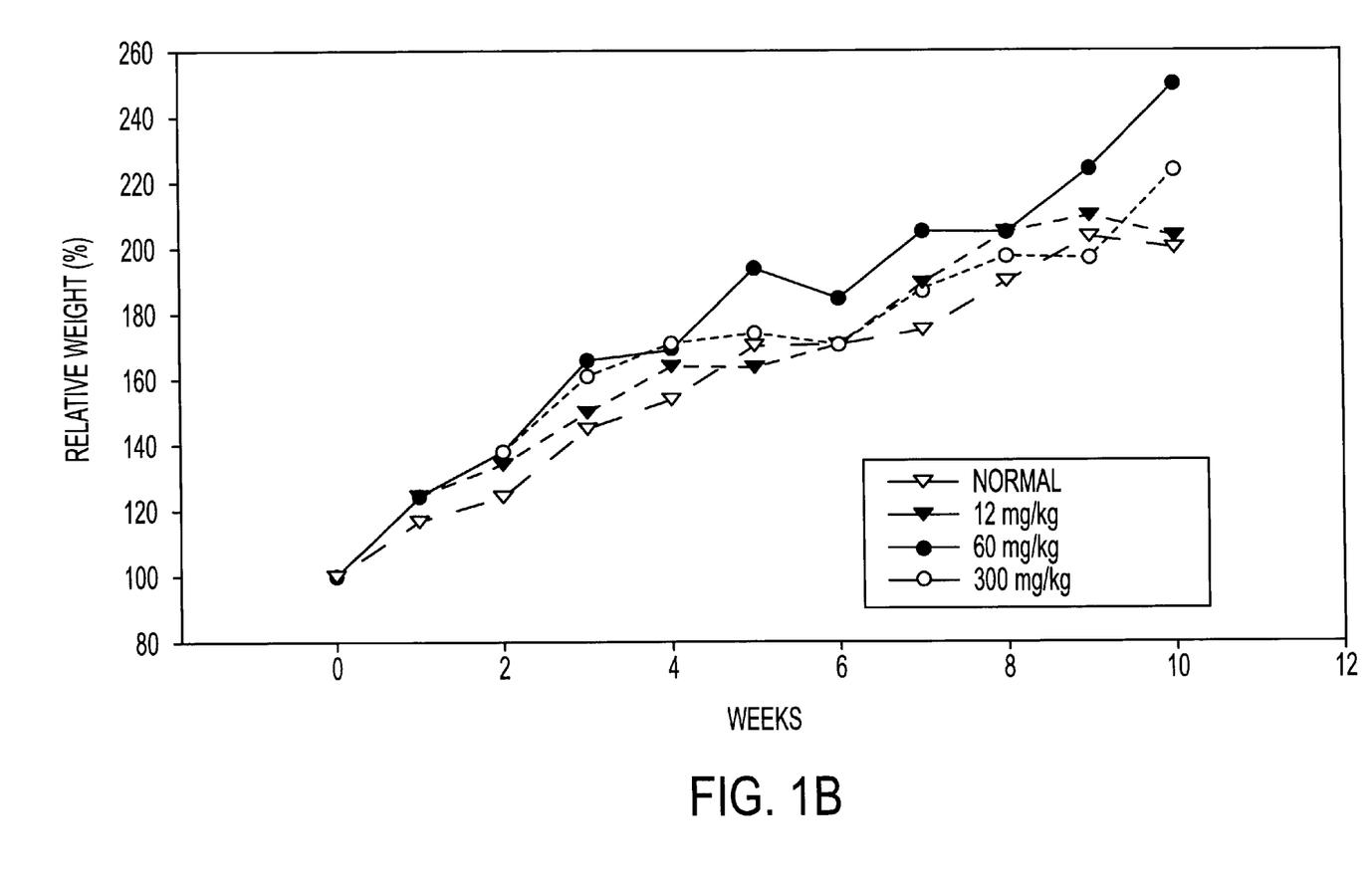
FIG. 1B shows the relative weight gain (%) in the rats after being given 0, 12 mg/kg, 60 mg/kg, and 300 mg/kg of the herbal composition. The results show that there were no significant differences in weight gain and food intake between the testing and control groups.
Figure 2:
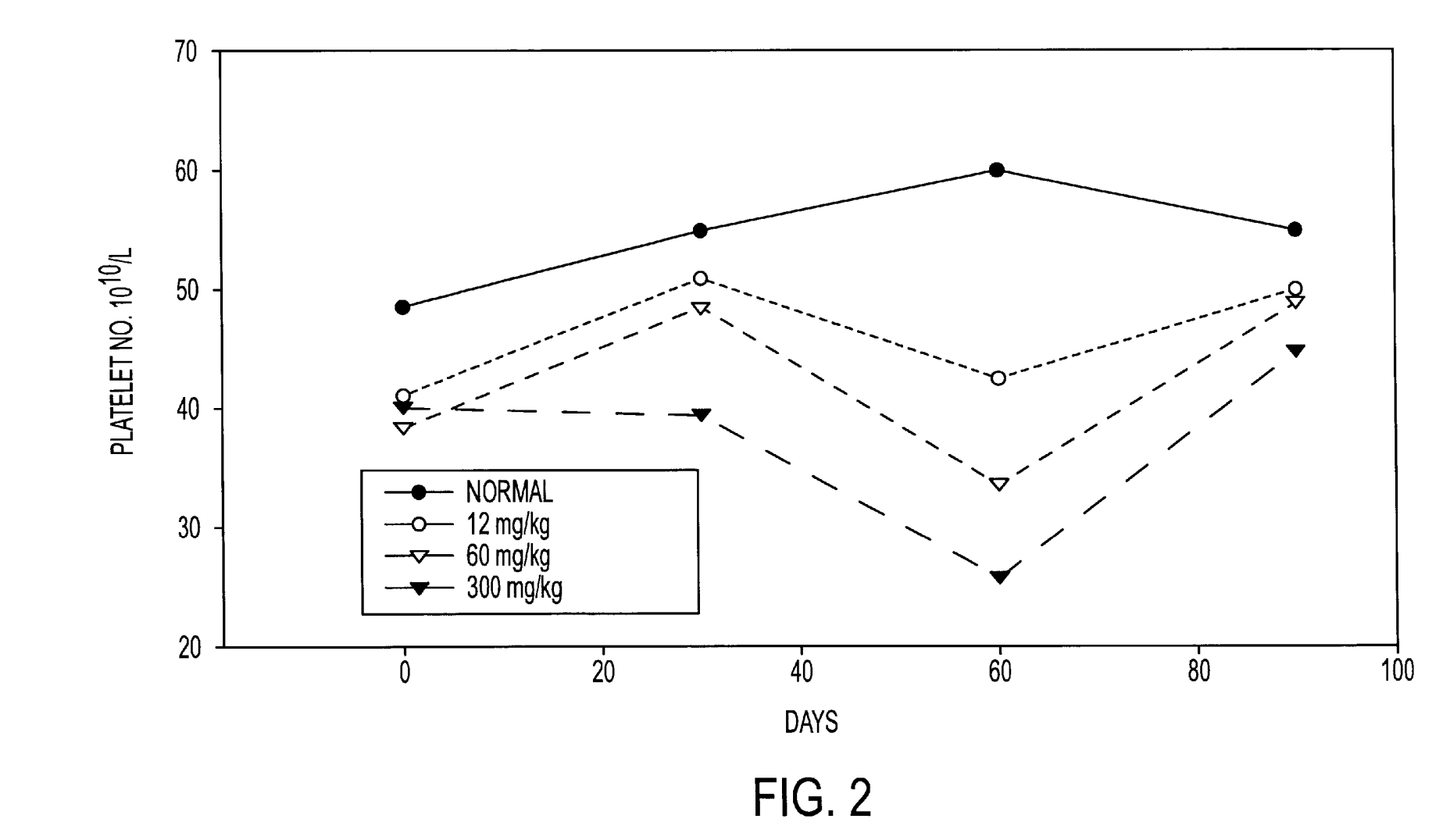

The appearance and behavior of the rats were normal. They were healthy and active and their appetite was good. The stools of the rats in the dosage groups were black and soft. There were no significant differences among groups on weight increase and food intake (FIGS. 1A and 1B). The nine parameters from blood and biochemical tests were within their normal ranges (Tables 1 and 2). At 30 days after ceasing the drug administration (i.e., day 90), two rats from the 60 mg/kg group and two rats from the 300 mg/kg group had a SGPT value higher than 70. However, no pathological change of the liver lobule or change of liver cells was observed under the microscopic examination of liver biopsy. The number of tissue red blood cells decreased as the rats became older, which might be a normal phenomenon during the development of bone marrow hematopoietic function. The number of platelets was within normal range. However, an orderly change among the groups was observed, that is, platelet counts decreased as the dosage increased (FIG. 2). Results from the ANOVA and paired t-tests indicated that there was no significant difference at day 30, but the difference was significant at day 60 and day 90.

The results showed that the number of the peripheral platelets started to decrease after receiving 300 mg/kg of this circulation-improving Chinese medicine for 30 days. At day 60, the platelet count of all three dosage groups decreased, which, however, rebound gradually 30 days after the cessation of administration.

TABLE 1

The Effects of Dosage on the Parameters of Blood and Biochemical Tests in Wistar Rats During Chronic Toxicity Test

|  | Dosage (mg/kg) | Day 0 | Day 30 | Day 60 | Day 90 |
|---|---|---|---|---|---|
| Hb (g/L) | 0 | 125.9 ± 12.2 | 147.8 ± 21.0 | 140.4 ± 8.7 | 143.6 ± 12.6 |
|  | 12 | 126.3 ± 10.0 | 153.4 ± 12.2 | 136.4 ± 10.5 | 143.9 ± 11.3 |
|  | 60 | 121.8 ± 25.2 | 146.1 ± 12.7 | 137.2 ± 10.6 | 146.8 ± 10.8 |
|  | 300 | 114.5 ± 26.6 | 143.8 ± 9.9 | 136.7 ± 9.2 | 150.0 ± 10.2 |
| RBC ($\times 10^{12}$/L) | 0 | 5.28 ± 1.11 | 5.64 ± 1.03 | 6.69 ± 1.96 | 6.89 ± 0.84 |
|  | 12 | 5.50 ± 1.62 | 5.84 ± 1.86 | 6.67 ± 0.68 | 7.13 ± 0.64 |
|  | 60 | 6.14 ± 0.79 | 5.58 ± 1.05 | 6.81 ± 1.03 | 7.13 ± 0.71 |
|  | 300 | 5.39 ± 1.30 | 6.20 ± 0.84 | 6.52 ± 0.68 | 7.05 ± 0.64 |
| Platelet ($\times 10^9$/L) | 0 | 489.0 ± 218.0 | 546.0 ± 229.2 | 592.5 ± 174.7 | 560.0 ± 107.8 |
|  | 12 | 411.6 ± 145.2 | 506.0 ± 230.0 | 425.5 ± 120.0 | 490.0 ± 128.7 |
|  | 60 | 390.5 ± 141.4 | 480.5 ± 210.0 | 327.2 ± 88.9 | 477.7 ± 93.1 |
|  | 300 | 405.5 ± 139.7 | 395.5 ± 113.9 | 262.7 ± 86.4 | 446.0 ± 113.9 |
| WBC ($\times 10^9$/L) | 0 | 7.23 ± 1.56 | 9.28 ± 0.85 | 6.78 ± 1.84 | 8.74 ± 1.41 |
|  | 12 | 6.15 ± 2.50 | 9.56 ± 0.94 | 6.69 ± 1.38 | 9.17 ± 1.90 |
|  | 60 | 6.24 ± 0.76 | 9.10 ± 0.99 | 6.87 ± 0.65 | 9.02 ± 1.63 |
|  | 300 | 6.04 ± 0.79 | 9.33 ± 0.94 | 6.21 ± 2.14 | 7.86 ± 1.47 |
| RTC (%) | 0 | 2.07 ± 2.57 | 0.73 ± 0.40 | 0.59 ± 0.32 | 0.70 ± 0.49 |
|  | 12 | 2.08 ± 1.72 | 0.65 ± 0.43 | 1.06 ± 0.63 | 0.51 ± 0.33 |
|  | 60 | 2.24 ± 1.12 | 0.72 ± 0.54 | 0.75 ± 0.55 | 0.59 ± 0.38 |
|  | 300 | 2.18 ± 1.28 | 0.71 ± 0.52 | 0.85 ± 0.92 | 0.50 ± 0.39 |
| PCV (%) | 0 | 42.65 ± 3.39 | 43.15 ± 3.63 | 44.23 ± 4.04 | 43.40 ± 5.42 |
|  | 12 | 42.90 ± 2.81 | 43.30 ± 3.75 | 42.80 ± 2.98 | 42.65 ± 4.57 |

TABLE 1-continued

The Effects of Dosage on the Parameters of Blood and
Biochemical Tests in Wistar Rats During Chronic Toxicity Test

|  | Dosage (mg/kg) | Day 0 | Day 30 | Day 60 | Day 90 |
|---|---|---|---|---|---|
|  | 60 | 43.15 ± 4.01 | 42.75 ± 2.40 | 43.38 ± 2.61 | 43.44 ± 2.70 |
|  | 300 | 43.35 ± 3.31 | 43.40 ± 2.60 | 43.26 ± 3.03 | 43.47 ± 3.27 |
| SGPT (U) | 0 | 45.89 ± 15.86 | 35.09 ± 10.17 | 23.55 ± 12.54 | 30.20 ± 14.20 |
|  | 12 | 44.75 ± 13.26 | 37.50 ± 12.02 | 22.80 ± 14.42 | 43.10 ± 10.95 |
|  | 60 | 47.00 ± 16.47 | 33.21 ± 13.02 | 27.28 ± 18.32 | 49.71 ± 17.23 |
|  | 300 | 44.50 ± 11.51 | 23.70 ± 7.46 | 24.31 ± 17.96 | 47.00 ± 20.41 |
| BUN (mmol/L) | 0 | 5.89 ± 2.32 | 6.77 ± 3.44 | 5.22 ± 0.84 | 7.44 ± 0.74 |
|  | 12 | 5.02 ± 2.07 | 7.20 ± 2.12 | 5.84 ± 0.77 | 7.57 ± 1.07 |
|  | 60 | 5.53 ± 2.15 | 5.06 ± 0.76 | 6.04 ± 0.91 | 7.21 ± 0.71 |
|  | 300 | 6.32 ± 2.30 | 5.32 ± 2.13 | 5.81 ± 0.92 | 7.49 ± 0.60 |

TABLE 2

The Effects of Dosage on the Ratio of Neutrophils, Lymphocytes,
Monocytes to Total White Blood Cells ($x \pm SD$) in Wistar Rats
During Chronic Toxicity Test

|  | Dosage (mg/kg) | Day 0 | Day 30 | Day 60 | Day 90 |
|---|---|---|---|---|---|
| Neutrophils (%) | 0 | 18.2 ± 11.6 | 38.4 ± 21.6 | 19.7 ± 8.7 | 24.2 ± 6.5 |
|  | 12 | 20.1 ± 10.7 | 32.1 ± 19.0 | 29.0 ± 15.8 | 26.9 ± 7.7 |
|  | 60 | 23.8 ± 8.2 | 25.1 ± 8.8 | 35.0 ± 17.5 | 27.3 ± 4.6 |
|  | 300 | 24.2 ± 12.9 | 29.6 ± 14.6 | 37.9 ± 19.5 | 29.4 ± 8.7 |
| Lymphocytes (%) | 0 | 79.0 ± 11.4 | 73.2 ± 7.8 | 75.7 ± 10.0 | 72.9 ± 7.0 |
|  | 12 | 77.1 ± 11.6 | 70.9 ± 14.8 | 66.8 ± 16.9 | 70.2 ± 8.2 |
|  | 60 | 72.5 ± 8.7 | 69.7 ± 8.6 | 63.3 ± 17.2 | 71.1 ± 5.8 |
|  | 300 | 71.3 ± 14.2 | 66.4 ± 14.8 | 59.8 ± 18.9 | 67.2 ± 8.7 |
| Monocytes (%) | 0 | 2.9 ± 2.0 | 2.0 ± 1.7 | 4.3 ± 2.5 | 3.3 ± 1.8 |
|  | 12 | 2.9 ± 1.8 | 4.1 ± 2.5 | 4.4 ± 2.5 | 3.1 ± 1.8 |
|  | 60 | 3.0 ± 1.9 | 5.2 ± 2.3 | 2.5 ± 1.8 | 2.4 ± 1.1 |
|  | 300 | 3.4 ± 2.6 | 4.0 ± 2.6 | 3.1 ± 1.8 | 2.9 ± 1.6 |

Pathological Examinations

There was no significant difference between the relative weight (g) of organs in different groups as shown in Table 3 and Table 4.

TABLE 3

The Relative Weight (g) ($x \pm SD$) (X10-2) of Organs After the
Subjects Have Received the Present Invention for 60 Days

| Organ | Dosage (mg/kg) | | | |
|---|---|---|---|---|
| (Gland) | 0 | 12 | 60 | 300 |
| Heart | 0.372 ± 0.088* | 0.335 ± 0.062 | 0.349 ± 0.060 | 0.378 ± 0.048 |
| Liver | 2.993 ± 0.301 | 2.774 ± 0.432 | 3.301 ± 0.502 | 3.388 ± 0.478 |
| Spleen | 0.207 ± 0.063 | 0.221 ± 0.043 | 0.227 ± 0.072 | 0.234 ± 0.028 |
| Lung | 0.524 ± 0.127 | 0.534 ± 0.106 | 0.524 ± 0.099 | 0.533 ± 0.081 |
| Kidney | 0.606 ± 0.029 | 0.581 ± 0.052 | 0.643 ± 0.062 | 0.651 ± 0.033 |
| Adrenal gland | 0.030 ± 0.010 | 0.028 ± 0.013 | 0.029 ± 0.010 | 0.030 ± 0.010 |
| Thyroid gland | 0.018 ± 0.003 | 0.017 ± 0.002 | 0.017 ± 0.003 | 0.017 ± 0.004 |
| Sexual gland ♂ | 0.987 ± 0.145 | 0.970 ± 0.135 | 0.953 ± 0.062 | 1.031 ± 0.303 |
| Sexual gland ♀ | 0.051 ± 0.030 | 0.070 ± 0.010 | 0.057 ± 0.013 | 0.076 ± 0.008 |

TABLE 4

The relative weight (g) ($x \pm SD$) (X10-2) of organs after the subjects have received the present invention for 90 days

| Organ (Gland) | Dosage (mg/kg) | | | |
|---|---|---|---|---|
| | 0 | 12 | 60 | 300 |
| Heart | 0.327 ± 0.059 | 0.354 ± 0.050 | 0.304 ± 0.175 | 0.309 ± 0.039 |
| Liver | 3.063 ± 0.295 | 3.195 ± 0.280 | 3.151 ± 0233 | 3.113 ± 0.351 |
| Spleen | 0.196 ± 0.048 | 0.222 ± 0.026 | 0.267 ± 0.022 | 0.210 ± 0.053 |
| Lung | 0.557 ± 0.134 | 0.594 ± 0.078 | 0.509 ± 0.081 | 0.479 ± 0.076 |
| Kidney | 0.608 ± 0.096 | 0.645 ± 0.054 | 0.620 ± 0.063 | 0.631 ± 0.054 |
| Adrenal gland | 0.034 ± 0.024 | 0.024 ± 0.010 | 0.022 ± 0.011 | 0.023 ± 0.007 |
| Thyroid gland | 0.010 ± 0.003 | 0.014 ± 0.003 | 0.013 ± 0.005 | 0.014 ± 0.004 |
| Sexual gland ♂ | 0.925 ± 0.058 | 0.910 ± 0.200 | 0.884 ± 0.064 | 0.909 ± 0.087 |
| Sexual gland ♀ | 0.051 ± 0.011 | 0.065 ± 0.012 | 0.045 ± 0.005 | 0.039 ± 0.006 |

The most common pathological changes found in gross and microscopic examinations were liver hydatid infection, idiopathy or malformation. None were associated with drug administration.

TABLE 5

Pathological Changes of the Organs

| Organ | Pathology | Dosage (mg/kg) | | | |
|---|---|---|---|---|---|
| | | 0 | 12 | 60 | 300 |
| Lungs | Bruise in the left lobes | | | | 1 |
| | Pulmonary edema | | 1 | | |
| | Pneumonia | 1 | | 1 | |
| Liver | Hydatid infection | 3 | 2 | 2 | 1 |
| Kidneys | Lacking one kidney | | | | 1 |
| Thyroid | Mal-development at one side | | | 1 | |

Four rats, two in the 60 mg/kg group and two in the 300 mg/kg group, died during the experiments. One of them dies from pussy chest, one with no known reason, and two from starving, weight loss and asthma (with no autopsy).

Determination of the levels of harmful elements: the results indicated that the levels of lead, arsenic, mercury in the present invention were substantially below their respective limit of detection.

III. Pharmacological Efficacy Tests

The therapeutic effects of the present invention confirmed by the pharmacological efficacy tests include:

1. Effects on the Blood Rheology

The present invention can improve the thickened, viscid, coagulant, and aggregating condition of the blood found in blood stasis. It is also beneficial for several parameters in the blood rheology. It decreases the whole blood viscosity, plasma viscosity, red blood cell aggregation, and platelet aggregation. It increases the velocity of red blood cell electrophoresis and slows down red blood cell precipitation to improve circulation.

The parameters in blood rheology were also improved significantly in 10 patients with transient ischemic attach (TIA) after orally administrating the medicine twice a day, 3 g each time for six months. The viscosity of the blood decreased from 13.02±2.78 cp to 11.67±2.01 cp; the time for red blood cell electrophoresis decreased from 25.07±2.31 s to 23.21±2.1 s; the average length of thrombus decreased from 28.35±12.31 mm to 22.31±2.87 mm, the average wet-weight and dry-weight decreased from 78.34±22.31 mg to 54.32±12.83 mg and from 18.63±8.72 mg to 13.21±2.67 mg, respectively during the in vitro thrombosis test. The platelet morphology from five patients was examined under an electronic microscope. The amount of the round-shaped and tree-liked platelets increased from 72.81±16.31% to 90.03±4.26% and the amount of the enlarged and aggregated platelets decreased from 27.82±12.16% to 9.07±5.13%, with a P-value<0.01. The results demonstrate that the present invention can improve the thickening, viscid, coagulant, and aggregating tendencies of the blood.

2. Effects on Hemodynamics

The present invention can increase cardiac contractility, improve myocardial metabolism, increase coronary blood flow, improve blood and oxygen supply to the myocardium and decrease myocardial oxygen consumption. It can also dilate the peripheral vessels to decrease blood pressure and improve the blood flow in the aorta and the downstream arteries to increase blood supply to the individual organs. Furthermore, it dilates the cerebral vessels to decrease vascular resistance and to increase blood volume in the brains.

The parameters in the cerebral hemodynamics of 10 patients with TIA treated with the present invention (orally administrated twice a day, 3 g each time for six months) were determined. The results are shown in Table 6:

TABLE 6

The Differences in the Values of the Parameters in Cerebral Hemodynamics Before and After the Treatment

| Parameter | n | Difference (X ± S) | t | P |
|---|---|---|---|---|
| Bloodflow | 10 | 1.58 ± 1.15 ml/min | 4.389 | <0.01 |
| Velocity | 10 | 1.77 ± 1.72 cl/min | 3.278 | <0.01 |
| Diameter of the carotid artery | 10 | 1.28 ± 1.08 mm | 3.765 | <0.01 |
| Peripheral resistance | 10 | 5460.44 ± 4340.85 dyn-sec/cm | 3.975 | <0.01 |
| Specific resistance | 10 | 878.61 ± 746.48 dynsec/cm | 3.719 | <0.01 |

The results confirmed that oral administration of the present composition increases blood flow volume and blood flow velocity in the brain and dilates vessels to decrease peripheral and specific resistance.

3. Effects on Micro-circulation

When there are significant changes in micro-circulation, the blood flow will change from the normal linear form or tape form into granulated, fluffy, dotted-line or broken-line forms. The blood cell aggregation will increase and small blood clots will form. Blood flow will slow down or even cease and thrombus begins to form. The present invention has good effects on the micro-circulation. Experiments have shown that administration of the d-polysaccharide improves conjunctival microcirculation of the eye in rabbits.

The present invention can improve the decreased diameter and spasm of arterioles, general dilation of the venules and sluggish blood flow velocity, change the fluffy blood flow into the tape-formed flow, and increase the blood flow velocity from 6.8 sec/mm before the treatment by 2.42 folds to 2.8 sec/mm (P-value<0.01).

4. The Effects in Acute Cerebral Ischemia Model

The acute cerebral ischemia in the guinea pig was induced by ligating the two lateral carotid arteries, which resulted in limpness of the body and the extremities, dilation and hyperemia of the blood vessels on the meninges, edema in the interstitial space around the vessels, swelling and transformation of the nucleus and cell membrane, dilation hyperemia of the arterioles at the choroid plexus. The present invention has been shown to improve these morphological changes of the brain tissues. In the clinical observation of 71 patients with ischemic stroke or TIA, 32 patients with ischemic stroke were administrated with the present invention twice a day (three times a day for severe cases) and 3 g each time; 39 patients with TIA were administrated with the present invention twice a day. After six months of treatment, 15 of the cases with ischemic stroke were cured, 9 showed significant improvement, 6 showed improvement and 2 were not affected. The total effective rate was 93.75%. In the 39 cases with TIA, 17 experienced no recurrence, and 19 experienced reduced frequency of onset, which represented an effective rate of 92.3%.

5. The Effects on the Plasma Prostaglandin

PGI2 and TXA2 are two metabolites of arachidonic acid in the prostaglandin metabolic pathway. The former can improve blood circulation while the later has the opposite effect. The present invention has been found to inhibit the synthesis of TXA2 and increase the amount of PGI2 in the blood. Fifteen patients of TIA were treated with the present invention twice a day and 3 g each time. After six months of treatment, the plasma content of TXB2 (the degraded product of TXA2) decreased by 19.06±14.589 pg/ml (P-value<0.01) and the content of 6-ketone-PGF1α (the degraded product of PGI2) increased by 25.95±8.29 pg/ml (P-value<0.01).

6. The Effects on the Levels of β-TG and PF4 in Cerebral Ischemia

Rabbits with ligations at both of the lateral carotid arteries were used as the model for acute cerebral ischemia. Ischemia caused significant increases in the levels of β-TG and PF4 in these animals. The increases were significantly reversed by the present invention. The levels for β-TG and PF4 were 85.61% and 47.59%, respectively, of the control values. These indicate that the present invention has multiple effects on the clotting factors released by the platelets and is beneficial for the biochemical system following ischemia.

The present invention has been shown to improve these morphological changes of the brain tissues. In the clinical observation of 71 patients with ischemic stroke or TIA, 32 patients with ischemic stroke were administrated with the present invention twice a day (three times a day for severe cases) and 3 g each time; 39 patients with TIA were administrated with the present invention twice a day. After six months of treatment, 15 of the cases with ischemic stroke were cured, 9 showed significant improvement, 6 showed improvement and 2 were not affected. The total effective rate was 93.75%. In the 39 cases with TIA, 17 experienced no recurrence, and 19 experienced reduced frequency of onset, which represented an effective rate of 92.3%.

7. The Effects on the Plasma Prostaglandin

PGI2 and TXA2 are two metabolites of arachidonic acid in the prostaglandin metabolic pathway. The former can improve blood circulation while the later has the opposite effect. The present invention has been found to inhibit the synthesis of TXA2 and increase the amount of PGI2 in the blood. Fifteen patients of TIA were treated with the present invention twice a day and 3 g each time. After six months of treatment, the plasma content of TXB2 (the degraded product of TXA2) decreased by 19.06±14.589 pg/ml (P-value<0.01) and the content of 6-ketone-PGF1α (the degraded product of PGI2) increased by 25.95 ±8.29 pg/ml (P-value<0.01).

8. The Effects on the Levels of β-TG and PF4 in Cerebral Ischemia

Rabbits with ligations at both of the lateral carotid arteries were used as the model for acute cerebral ischemia. Ischemia caused significant increases in the levels of β-TG and PF4 in these animals. The increases were significantly reversed by the present invention. The levels for β-TG and PF4 were 85.61% and 47.59%, respectively, of the control values. These indicate that the present invention has multiple effects on the clotting factors released by the platelets and is beneficial for the biochemical system following ischemia.

During the manufacturing process of the present invention, both the single-herbal extraction and combined herbal extraction had been used and various excipients had been tested to determine the most appropriate process and excipients which could provide the best quality, stability and efficacy of the drug.

The following examples are intended to illustrate the present invention in greater detail. They do not in any way limit the scope of the invention.

EXAMPLE 1

Method (1) Mixing the powder of 100 g Chuan Xiong, 80 g Dang Gui and 20 g Red Ginseng in an extraction tank;

(2) Adding 800 ml of 60% alcohol in the extraction tank followed by heating up the mixture for four hours;

(3) Filtering the mixture and collecting the first filtrate;

(4) (Optionally) Repeating steps (1) (i.e., by adding more alcohol to the herbal mixture that already had been extracted) to (3) to collect a second and a third filtrates;

(5) Mixing all the filtrates and putting the filtrates into a condensation tank for decompressed condensation until the volume of final extract has reduced to $\frac{1}{10}$ of the original filtrate to produce the extraction paste; and (6) Adding 400 g of the soluble starch and add the extraction paste slowly into the fluidized bed for the granulation process, which was proceeded with a heat-dry step.

In accordance with the steps described above, a final herbal composition with a dry weight of about 81.2 g in extract paste was produced. The water content of the final herbal composition was tested to determine the necessary drying time. The water content has to be lower than 3.5%, which indicates the completion of granulation. The granules were then sorted through a no. 20 mesh, before being packed, inspected and packaged.

Results

The final herbal composition and standard products were quantitatively analyzed and compared using High Performance Liquid Chromatography (HPLC). The results showed that the concentration of ferulic acid was 0.02%, disintegration time was 3 minutes, water content was 4%, pH 5.7, and lead and arsenic levels were within the limit of detection.

EXAMPLE 2

Method
(1) Respectively, mixing 120 g Chuan Xiong with 500 ml of 60% alcohol; 100 g Dang Gui with 400 ml of 60% alcohol; and 20 g Red Ginseng with 100 ml of 60% alcohol, each in a separate extraction tank;
(2) Individually heating up each of the herbs in alcohol in the respective extraction tank for four hours;
(3) Separately filtering each of the herbal extracts to collect a first filtrate from each herb;
(4) (Optionally) Repeating steps (1) (i.e., by adding more alcohol to the remaining herb) to (4) to collect a second and a third filtrates from each of the extraction tanks, respectively;
(5) Mixing all of the respective filtrates together and putting the filtrates into a condensation tank for decompressed condensation until the volume of each of the respective final extracts has reduced to 1/10 of the original filtrates to produce an extraction paste;
(6) Proceeding with granulation, followed by sifting and sorting with a no.20 mesh before underwent packing, inspection, and packaging and for quality control as described in Example 1.

Results

Analysis of the product indicates that the concentration of ferulic acid was 0.032%, disintegration time was 3.5 minutes, water content was 3.8%, pH 6.5, and the level of lead and arsenic were within limit of detection.

While the invention has been described by way of examples and in terms of the preferred embodiments, it is to be understood that the invention is not limited to the disclosed embodiments. On the contrary, it is intended to cover various modifications as would be apparent to those skilled in the art. Therefore, the scope of the appended claims should be accorded the broadest interpretation so as to encompass all such modifications.

We claim:

1. An herbal composition comprising an extract of 30–50 wt % of Dang Gui root (Radix Angelicae sinensis), 35–65 wt % of Chuan Xiong root (Radix Ligustici Chuanxiong), and 7–13 wt % of root of Ginseng root (Radix Ginseng), wherein said Dang Gui root, Chuan Xiong root, and Ginseng root are extracted by an extractant which contains alcohol and water.

2. The herbal composition according to claim 1, wherein Dang Gui is 33–45 wt %, Chuan Xiong is 42–58 wt %, and Ginseng is 8–12 wt %.

3. The herbal composition according to claim 1, wherein said Ginseng is Red Ginseng (Radix Ginseng Rubra).

4. The herbal composition according to claim 1, wherein said herbal composition improves blood circulation.

5. The herbal composition according to claim 1, wherein said herbal composition is used to treat patients with stroke.

6. A method for improving blood circulation comprising orally administering an effective amount of the herbal composition according to claim 1 to humans.

7. A method for treating patients with stroke comprising orally administering an effective amount of the herbal composition according to claim 1 to said patients with stroke.

8. A process for preparing the herbal composition according to claim 1, comprising:
a) mixing said Dang Gui root, said Chuan Xiong root, and said Ginseng root to form an herbal mixture;
b) adding an extractant to the herbal mixture to form an herbal mixture extract;
c) heating the herbal mixture extract;
d) filtering the heated herbal mixture extract to obtain a filtrate;
e) putting said filtrate into a condensation tank for decompressed condensation to obtain an extraction paste; and
f) granulating said extraction paste to form granules.

9. The process according to claim 8, wherein after the filtrate was obtained, said Dang Gui root, said Chuan Xiong root, and said Ginseng root are further extracted by repeating the steps of b)–d) to form a second filtrate; said second filtrate being combined with the filtrate.

10. The process according to claim 9, wherein after the second filtrate was obtained, said Dang Gui root, said Chuan Xiong root, and said Ginseng root are further extracted by repeating the steps of b)–d) to form a third filtrate; said third filtrate being combined with the filtrate and the second filtrate.

11. The process according to claim 8, wherein said extraction paste comprises about 1/10 (v/v) of the filtrate.

12. The process according to claim 8, wherein said extraction paste is mixed with a soluble starch before granulation.

13. The process according to claim 8, wherein said granules are capsulated.

14. The process according to claim 8, wherein said extraction paste comprises 0.5 to 2.8 mg of ferulic acid per gram of said extraction paste.

15. The process according to claim 8, wherein said extraction paste comprises 0.2 to 1.6 mg of tetra-methyl pyrazine per gram of said extraction paste.

16. The process according to claim 8, wherein said granules comprise 0.08 to 0.42 mg of ferulic acid per gram of said granules.

17. The process according to claim 8, wherein said granules comprises 0.04 to 0.25 mg of tetra-methyl pyrazine per gram of said granules.

18. A process for preparing an herbal composition according to claim 1, comprising:
a) extracting said Dang Gui root, said Chuan Xiong root, and said Ginseng root by adding an extractant to said Dang Gui root, said Chuan Xiong root, and said Ginseng root respectively to form a Dang Gui root extract, a Chuan Xiong root extract, and a Ginseng root extract;
b) heating said Dang Gui root extract, said Chuan Xiong root extract, and said Ginseng root extract;
c) filtering the heated Dang Gui root extract, the heated Chuan Xiong root extract, and the heated Ginseng root extract to obtain a Dang Gui filtrate, a Chuan Xiong filtrate and a Ginseng filtrate;
d) mixing the Dang Gui filtrate, the Chuan Xiong filtrate and the Ginseng filtrate to form a final filtrate;
e) putting said final filtrate into a condensation tank for decompressed condensation to obtain an extraction paste; and
f) granulating said extraction paste to form granules.

19. The process according to claim 18, wherein after said Dang Gui root filtrate, said Chuan Xiong filtrate, and said Ginseng filtrate were obtained, said Dang Gui root, said Chuan Xiong root, and said Ginseng root are further extracted respectively by repeating steps a) to c) to form a second Dang Gui filtrate, a second Chuan Xiong filtrate, and a second Ginseng filtrate; said second Dang Gui filtrate, said second Chuan Xiong filtrate, and said second Ginseng filtrate being added to the final filtrate.

20. The process according to claim 19, wherein after said second Dang Gui root filtrate, said second Chuan Xiong filtrate, and said second Ginseng filtrate were obtained, said Dang Gui root, said Chuan Xiong root, and said Ginseng root are further extracted respectively by repeating steps a) to c) to form a third Dang Gui filtrate, a third Chuan Xiong filtrate, and a third Ginseng filtrate; said third Dang Gui filtrate, said third Chuan Xiong filtrate, and said third Ginseng filtrate being added to the final filtrate.

21. The process according to claim 18, wherein said extraction paste comprises about 1/10 (v/v) of the final filtrate.

22. The process according to claim 18, wherein said extraction paste is mixed with a soluble starch before granulation.

23. The process according to claim 18, wherein said granules are capsulated.

24. The process according to claim 18, wherein said extraction paste comprises 0.5 to 2.8 mg of ferulic acid per gram of said extraction paste.

25. The process according to claim 18, wherein said extraction paste comprises 0.2 to 1.6 mg of tetra-methyl pyrazine per gram of said extraction paste.

26. The process according to claim 18, wherein said granules comprise 0.08 to 0.42 mg of ferulic acid per gram of said granules.

27. The process according to claim 18, wherein said granules comprises 0.04 to 0.25 mg of tetra-methyl pyrazine per gram of said granules.

* * * * *